(12) United States Patent
Vitushinsky et al.

(10) Patent No.: US 9,675,262 B2
(45) Date of Patent: Jun. 13, 2017

(54) 2DEG-BASED SENSOR AND DEVICE FOR ECG SENSING

(71) Applicant: Stichting IMEC Nederland, Eindhoven (NL)

(72) Inventors: Roman Vitushinsky, Vaals (NL); Peter Offermans, Eindhoven (NL)

(73) Assignee: Stichting IMEC Nederland, Eindhoven (NL)

( * ) Notice: Subject to any disclaimer, the term of this patent is extended or adjusted under 35 U.S.C. 154(b) by 141 days.

(21) Appl. No.: 14/265,088

(22) Filed: Apr. 29, 2014

(65) Prior Publication Data
US 2014/0323895 A1 Oct. 30, 2014

(30) Foreign Application Priority Data
Apr. 29, 2013 (EP) ..................... 13165848

(51) Int. Cl.
*A61B 5/0408* (2006.01)
*H01L 27/088* (2006.01)
(Continued)

(52) U.S. Cl.
CPC ......... *A61B 5/0408* (2013.01); *G01N 27/129* (2013.01); *G01N 27/414* (2013.01);
(Continued)

(58) Field of Classification Search
CPC ....... H01L 2924/00; H01L 2924/13091; H01L 2924/13062; H01L 2224/45124;
(Continued)

(56) References Cited

U.S. PATENT DOCUMENTS

| 8,148,830 B2 * | 4/2012 | Bedinger ............ H01L 23/3192 257/790 |
| 2006/0060871 A1 * | 3/2006 | Beach ................. H01L 29/0623 257/94 |

(Continued)

FOREIGN PATENT DOCUMENTS

WO WO 2012/054683 4/2012

OTHER PUBLICATIONS

Cui et al., Novel ESD protection solution for single-ended mixer in GaAs pHEMT technology, Apr. 20, 2013 Microelectronics Reliability, 53, 952-955.*

(Continued)

*Primary Examiner* — Marc Armand
*Assistant Examiner* — Shannon Yi
(74) *Attorney, Agent, or Firm* — Knobbe, Martens, Olson & Bear LLP (57) ABSTRACT

The disclosed technology generally relates to sensors comprising a two-dimensional electron gas (2DEG), and more particularly to an AlGaN/GaN 2DEG-based sensor for sensing signals associated with electrocardiograms, and methods of using the same. In one aspect, a sensor comprises a substrate and a GaN/AlGaN hetero-junction structure formed on the substrate and configured to form a two-dimensional electron gas (2DEG) channel within the GaN/AlGaN hetero-junction structure. The sensor additionally comprises Ohmic contacts connected to electrical metallizations and to the 2DEG channel, wherein the GaN/AlGaN hetero-junction structure has a recess formed between the Ohmic contacts. The sensor further comprises a dielectric layer formed on a top surface of the sensor.

20 Claims, 11 Drawing Sheets

(51) Int. Cl.
　　　H01L 29/778　　(2006.01)
　　　H01L 29/423　　(2006.01)
　　　G01N 27/12　　(2006.01)
　　　G01N 27/414　　(2006.01)
　　　A61B 5/021　　(2006.01)
　　　A61B 5/0452　　(2006.01)
　　　A61B 5/00　　(2006.01)
(52) U.S. Cl.
　　　CPC ........ *H01L 27/088* (2013.01); *H01L 29/4236* (2013.01); *H01L 29/42372* (2013.01); *H01L 29/7786* (2013.01); *A61B 5/02125* (2013.01); *A61B 5/0452* (2013.01); *A61B 5/6824* (2013.01)
(58) Field of Classification Search
　　　CPC . H01L 2224/48227; H01L 2224/73265; H01L 2924/12032; H01L 2224/32145; H01L 2924/1461
　　　See application file for complete search history.

(56) References Cited

U.S. PATENT DOCUMENTS

| | | | | |
|---|---|---|---|---|
| 2009/0072272 | A1* | 3/2009 | Suh | H01L 29/1066 257/194 |
| 2009/0306732 | A1* | 12/2009 | Rosenberg | A61B 5/0422 607/9 |
| 2011/0088456 | A1* | 4/2011 | Ren | G01N 33/005 73/31.06 |
| 2011/0199102 | A1* | 8/2011 | Garcia | G01N 27/4148 324/658 |
| 2011/0220965 | A1* | 9/2011 | Ohki | H01L 21/28264 257/194 |
| 2012/0149161 | A1* | 6/2012 | Ohki | H01L 29/7786 438/270 |
| 2014/0210835 | A1* | 7/2014 | Hong | H01L 29/78696 345/530 |

OTHER PUBLICATIONS

Hung et al., "Detection of chloride ions using an integrated Ag/AgCl electrode with AlGaN/GaN high electron mobility transistors," *AIP Applied Physics Letters*, vol. 92, 193903 (2008).

Kim et al., "Effects of TMAH Treatment on Device Performance of Normally Off $Al_2O_3$/GaN MOSFET," *IEEE Electron Device Letters*, vol. 32, No. 10, pp. 1376-1378 (Oct. 2011).

Kim et al., "Miniaturized One-Point Detectable Electrocardiography Sensor for Portable Physiological Monitoring Systems," *IEEE Sensors Journal*, vol. 12, No. 7, pp. 2423-2424 (Jul. 2012).

Maruyama et al., "ECG Measurement Using Capacitive Coupling Electrodes for Man-Machine Emotional Communication," IEEE/ICME International Conference on Complex Medical Engineering, 1-4244-1078-9/07, pp. 378-383 (2007).

Offermans et al., "Ultra-Sensitive $NO_2$ Detection with AlGaN/GaN 2DEG Channels for Air Quality Monitoring," *IEEE* 978-1-4577-1767-3/12, 3 pps (2012).

* cited by examiner

2DEG-BASED SENSOR AND DEVICE FOR ECG SENSING

CROSS-REFERENCE TO RELATED APPLICATIONS

This application claims foreign priority to European patent application EP 13165848.6 filed on Apr. 29, 2013, the content of which is incorporated by reference herein in its entirety.

BACKGROUND OF THE INVENTION

Field of the Invention

The disclosed technology generally relates to sensors comprising a two-dimensional electron gas (2DEG), and more particularly to an AlGaN/GaN 2DEG-based sensor and a device for sensing signals associated with electrocardiograms, and methods of using the same.

Description of the Related Technology

Heterostructures based on aluminium gallium nitride/gallium nitride (AlGaN/GaN) show great promise as a generic platform for the development of high performance sensing devices that offer direct electrical readout. These devices employ the sensitivity of the highly mobile 2DEG formed at the interface of the AlGaN/GaN heterostructure to changes in the polarization or surface charge. 2DEG-based biochemical sensors have been used for the detection of gases, polar liquids, pH, proteins and DNA.

Some known 2-DEG based sensors are described, for example, in international patent application WO 2012/054683 and in papers "*Ultra-Sensitive NO2 Detection with AlGaN/GaN 2DEG Channels for Air Quality Monitoring*", P. Offermans et al., IEEE Sensors Journal 2012, Date of Conference: 28-31 Oct. 2012, and "*Detection of chloride ions using an integrated Ag/AgCl electrode with AlGaN/GaN high electron mobility transistors*", S. C. Hung et al., Applied Physics Letters 92, 14 May 2008.

SUMMARY OF CERTAIN INVENTIVE ASPECTS

According to exemplary embodiments disclosed herein, AlGaN/GaN 2DEG-based sensors can be used for detecting, measuring and monitoring various signals associated with an electrocardiogram (ECG). Advantageously, according to the various embodiments, the ECG detection comprises a charge-based non-differential ECG detection. Advantageously, according to the various embodiments, the sensors make ECG detection possible on a single body point, e.g., at a single skin point. According to some exemplary embodiments, the 2DEG-based sensitive structures can be placed on a single skin point, for example at the chest or on the wrist, by placing, e.g., the 2DEG-based sensitive structures inside a patch-worn or a wrist-worn device worn at certain sufficiently close proximity from the body.

In one aspect, a sensor comprises a substrate and a GaN/AlGaN hetero-junction structure formed on the substrate and configured to form a two-dimensional electron gas (2DEG) channel within the GaN/AlGaN hetero-junction structure. The sensor additionally comprises Ohmic contacts connected to electrical metallizations and to the 2DEG channel, wherein the GaN/AlGaN hetero-junction structure has a recess formed between the Ohmic contacts. The sensor further comprises a dielectric layer formed on a top surface of the sensor.

According to an exemplary embodiment, the sensor may further comprise a layer of an extended gate material placed on top of the dielectric layer and in the GaN/AlGaN hetero-junction recessed area.

According to another exemplary embodiment, the sensor may further comprise an electrode stack on top of the extended gate material.

In another aspect, a device for ECG detection comprises an AlGaN/GaN 2DEG-based sensor according to any of the embodiments herein described. According to exemplary embodiments, the device is advantageously suitable for ECG, atrial-ventricular heart polarization cycles and/or blood pressure (BP) monitoring.

According to an exemplary embodiment, a device for ECG sensing comprises a sensor according to any of the embodiments herein described which is arranged so that the GaN/AlGaN hetero-junction recessed area, the extended gate material or the electrode stack is in direct contact or sufficiently close to a certain body skin point such that, during an ECG P-QRS-T complex pulse, the skin electrical potential and intra or extra cellular ionic micro currents interact with the 2DEG channel causing its conductivity to change. According to an exemplary embodiment, the device for ECG sensing comprises a plurality of such sensors connected in series or in parallel for combined ECG detection. According to an exemplary embodiment, the device for ECG sensing comprises at least one sensor which is under the influence of a magnetic field arranged in such a way to influence the ECG detection sensitivity. According to an exemplary embodiment, the device for ECG sensing may be further configured for calculating a blood pressure (BP) value based on ECG detection. According to an exemplary embodiment, the device for ECG sensing may be a patch-worn or wrist-worn device for ECG sensing.

In another aspect, use of a sensor according to any of the embodiments described herein for ECG detection comprises applying the sensor in direct contact or sufficiently close to a certain body skin point.

In yet another aspect, a method for ECG detection comprises: applying a sensor according to any of the embodiments herein described such that that the GaN/AlGaN hetero-junction recessed area, the extended gate material or the electrode stack is in direct contact or close to a certain living being's body skin so that the skin electrical charge and intra or extra cellular ionic micro currents interact with the sensor's 2DEG channel; and detecting a conductivity change within the 2DEG channel during an ECG P-QRS-T complex of a living being.

Certain objects and advantages of various new and inventive aspects have been described above. It is to be understood that not necessarily all such objects or advantages may be achieved in accordance with any particular embodiment of the present invention. Those skilled in the art will recognize that the solution of the present invention may be embodied or carried out in a manner that achieves or optimizes one advantage or group of advantages without necessarily achieving other objects or advantages.

BRIEF DESCRIPTION OF THE DRAWINGS

The above and other aspects of the AlGaN/GaN 2DEG-based sensor and device for ECG sensing according to the present invention will be shown and explained with reference to the non-restrictive example embodiments described hereinafter.

DETAILED DESCRIPTION OF CERTAIN ILLUSTRATIVE EMBODIMENTS

In the following, in the description of exemplary embodiments, various features may be grouped together in a single embodiment, figure, or description thereof for the purpose of streamlining the disclosure and aiding in the understanding of one or more of the various inventive aspects. This is however not to be interpreted as the invention requiring more features than the ones expressly recited in the main claim. Furthermore, combinations of features of different embodiments are meant to be within the scope of the invention, as would be clearly understood by those skilled in the art. Additionally, in other instances, well-known methods, structures and techniques have not been shown in detail in order not to obscure an understanding of the description.

Figure 1A:
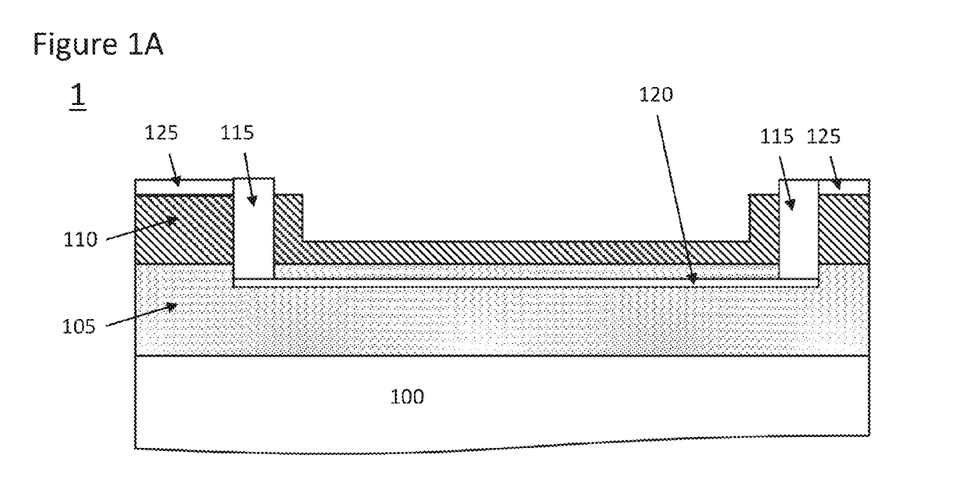
FIGS. 1A and 1B illustrate a cross-sectional view of AlGaN/GaN 2DEG-based sensors according to some embodiments.

FIG. 1A shows an AlGaN/GaN 2DEG-based sensor 1, comprising a substrate layer 100, a GaN layer 105, an AlGaN layer 110, Ohmic contacts 115, a 2DEG channel 120, and electrical metallizations 125, according to some embodiments.

According to the illustrated embodiments, the sensor 1 comprises a GaN/AlGaN hetero-junction with a two-dimensional electron gas (2DEG) channel 120 close to the interface between GaN layer 105, which can be a buffer layer, and the AlGaN layer 110, which can be a barrier layer. Advantageously, the AlGaN layer 110 may be either recessed or formed, e.g., grown, as a thin layer between the Ohmic contacts 115, thus forming an open gate layout. According to an exemplary embodiment of the invention, the AlGaN layer 110 may be recessed between the Ohmic contacts 115 such that the AlGaN layer 110 has a thickness between about 5 nm and about to 8 nm Ohmic. According to another exemplary embodiment of the invention, the AlGaN layer 110 may be formed, e.g., grown, as a thin layer having a thickness between about 6 nm and about 8 nm between the Ohmic contacts 115. The thickness of the AlGaN layer 110 can be correlated to the charge sensitivity of the 2DEG channel 120, and having the thickness to be in the range between about 5 nm and about 8 nm, or between about 6 nm and about 8 nm, can be advantageous for optimizing the charge sensitivity of the 2DEG channel 120 for particular applications disclosed herein. The electrical metallizations 125 may comprise a suitable metallization that allows the flow of electric current to/from the Ohmic contacts 115, which also contact the 2DEG channel 120. The substrate layer 100 may comprise a suitable material for forming the GaN layer 105 thereon, including, for example, Si, SiC, Sapphire, GaN or AlN. When a potential difference is applied between the Ohmic contacts 115, a current flows through the 2DEG channel 120.

The 2DEG channel 120 formed near or at the GaN/AlGaN interface serves as a main sensitive element reacting to a surface charge and potential. According to an exemplary embodiment, the 2DEG channel 120 is configured to interact with very small variations in surface or proximal charge or changes of electrical field on AlGaN/liquid-gas or AlGaN/metal/liquid-gas interfaces interacting with the surface donor states of the AlGaN layer. Without being bound to any theory, surface donor states are considered to be the source of electrons in the formation of the 2DEG channel 120. These donor states may possess a wide distribution of ionization energies within the band gap and are caused by redox reactions, dangling bonds and vacancies in the surface layer. A balance exists between the 2DEG channel density and the number of ionized surface donors which is governed by charge neutrality and continuity of the electric field at the interfaces.

According to some embodiments, the AlGaN/GaN 2DEG-based sensor 1 may be used for detection of electrical field or changes in electrical charge. This can be advantageous, for example, for detection of heart dipole charges dynamics during a complete heart cycle from atrial depolarization to ventricular repolarization. According to an exemplary embodiment of the invention, the AlGaN/GaN 2DEG-based sensor 1 may be used to detect electrical heart charges created from heart as the electrical volume source enabling the heart function. The body charges may be detected, for example, by placing the recessed gate or the recessed portion of the AlGaN layer 110, between the Ohmic contacts 115, at a close distance or in direct contact with the body skin in order to obtain ECG-activity detection. Advantageously, the location may be a single body skin point location and the ECG detection can be a charge-based non-differential ECG-time-equivalent detection.

According to some embodiments, by using a reference-electrode-free transistor-like measurement/operation (e.g. ISFET-like) with current flowing between two Ohmic contacts (source-drain), a single skin point ECG detection is possible, avoiding the need to apply separated sensing electrodes at two body points. According to an exemplary embodiment, the sensor 1 is coupled to a certain body skin point within a sufficiently close proximity, e.g., in direct contact, such that, during the P-QRS-T heart dipole dynamics (an electrophysiological heart function polarization cycle), the electrical charge on the skin point interacts directly electrostatically and through the surface states with the 2DEG channel 120, thereby causing the conductivity of the 2DEG channel 120 to change. The interaction between the skin surface and the 2DEG channel 120 occurs electrostatically via electric field in a manner similar to an interaction between a gate electrode and the 2DEG channel 120, by causing ionisation or energy shift of the surface states of AlGaN barrier layer 110.

According to exemplary embodiments, there a gas, such as for example air, a liquid, such as for example water or sweat, or a gel may be provided between the sensor 1 and the body skin surface to enhance the detection.

Figure 1B:
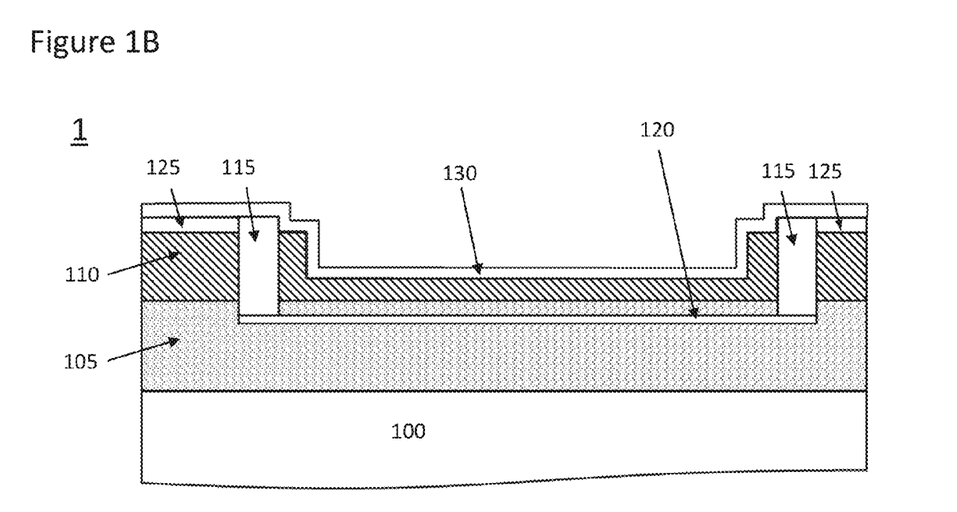

FIG. 1B shows another AlGaN/GaN 2DEG-based sensor 1 according to some embodiments, comprising a substrate layer 100, a GaN layer 105, an AlGaN layer 110, Ohmic contacts 115, a 2DEG channel 120, electrical metallizations 125, and a dielectric layer 130.

The sensor 1 of FIG. 1B is similar to the sensor 1 described with respect to FIG. 1A, except that the sensor 1 of FIG. 1B further comprises a dielectric layer 130 formed over, e.g., on a top surface of the sensor 1 such that the dielectric layer 130 is configured to be coupled to a certain body skin point within a sufficiently close proximity, e.g., in direct contact, such that, during an electrophysiological heart function polarization cycle, the electrical body charge interacts with the 2DEG channel and causes a conductivity of the 2DEG channel 120 to change. The dielectric layer 130 can advantageously be configured to prevent leakage currents to flow directly between the skin and the 2DEG channel 120. In addition, the dielectric layer 130 can advantageously be configured to enhance sensitivity of detection of certain changes in the body. According to an exemplary embodiment, the dielectric layer 130 may have a thickness between about 3 nm and about 10 nm, and may be comprise, for example, aluminium oxide ($AlO_x$).

Figure 2A:
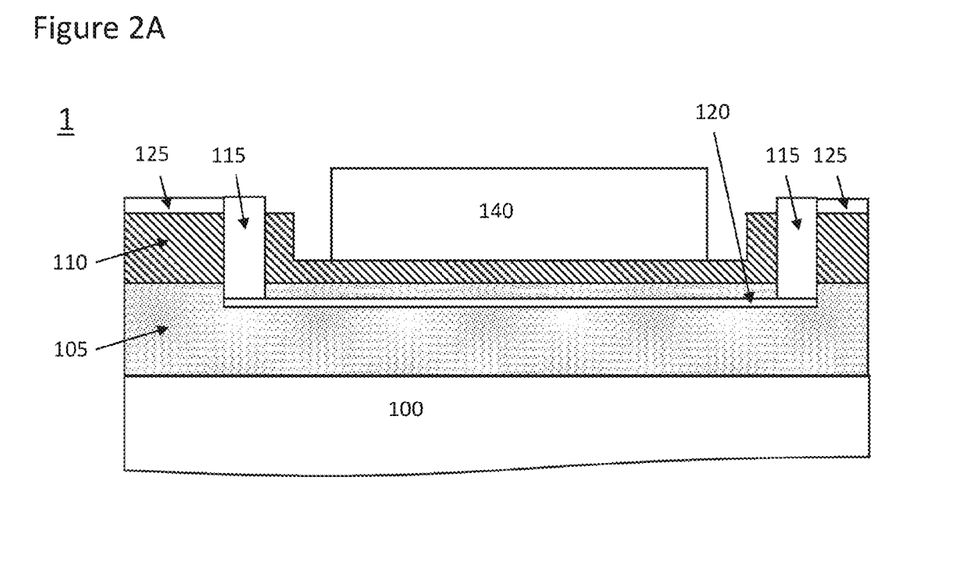
FIGS. 2A to 2C illustrate AlGaN/GaN 2DEG-based sensors according to some other embodiments.

FIG. 2A shows another AlGaN/GaN 2DEG-based sensor 1 according to some other embodiments, comprising a substrate layer 100, a GaN layer 105, an AlGaN layer 110, Ohmic contacts 115, a 2DEG channel 120, electrical metallizations 125, and an extended gate material 140.

The sensor 1 of FIG. 2A is similar to the sensor 1 described above with respect to FIG. 1A, except that the sensor 1 of FIG. 2A further comprises an additional gate material 140 formed over, e.g., on a top surface of the AlGaN layer 110, e.g., on the gate electrode, and configured to be coupled to a certain body skin point within a sufficiently close proximity, e.g., in direct contact, such that, during an electrophysiological heart function polarization cycle, the electrical body charge interacts with the 2DEG channel and causes a conductivity of the 2DEG channel 120 to change. The extended gate material 140 advantageously enhances the charge sensitivity of the 2DEG channel 120 by increasing the polarization field with an electrolyte (e.g. sweat or gel), creating a better electrical skin contact with dry skin or by increasing the charge transfer from the skin to the AlGaN gate surface. According to an exemplary embodiment, the extended gate material 140 may have a thickness selected to be between about 1 nm and about 1000 nm, and may comprise a suitable gate material including, for example, Au, Ag, Pt(Ox), Ir(Ox), PtIrOx or Ag/AgCl—quasi reference electrode stack.

According to some embodiments, it is possible to use as an extended charge-gating electrode another 2DEG-channel patterned close or electrically connected to a primary sensitive 2DEG-channel. The 2DEG-based extended gate is electrically connected to the body single point.

During an electrophysiological P-QRS-T heart dipole dynamics, intracellular ionic micro currents that can be caused by heart muscle polarization within the electrolyte-like volume conductive body tissue. According to an exemplary embodiment, a non-polarizable extended gate material 140 comprising a quasi-reference electrode (Ag/AgCl)-stack may be advantageously used in order to detect those micro currents with high sensitivity, which correspond with the ECG-activity. According to some embodiments, such gate material may be put in electrical contact with the body skin, for example in direct contact with the skin or via a gel, for reacting chemically with chloride ($Cl^-$) ions. The chloride concentration involved in ionic micro currents during an ECG-pulse will change, which can result in changes in the work function and surface potential of the Ag/AgCl extended gate material 140 deposited on the AlGaN layer 110, thus changing the ionisation and energy level of the surface states within AlGaN-barrier layer. According to some other embodiments, a chemically inert Au extended gate material 140 may be used to enhance the E-field interaction with the AlGaN layer 110 in dry and wet conditions.

Figure 2B:
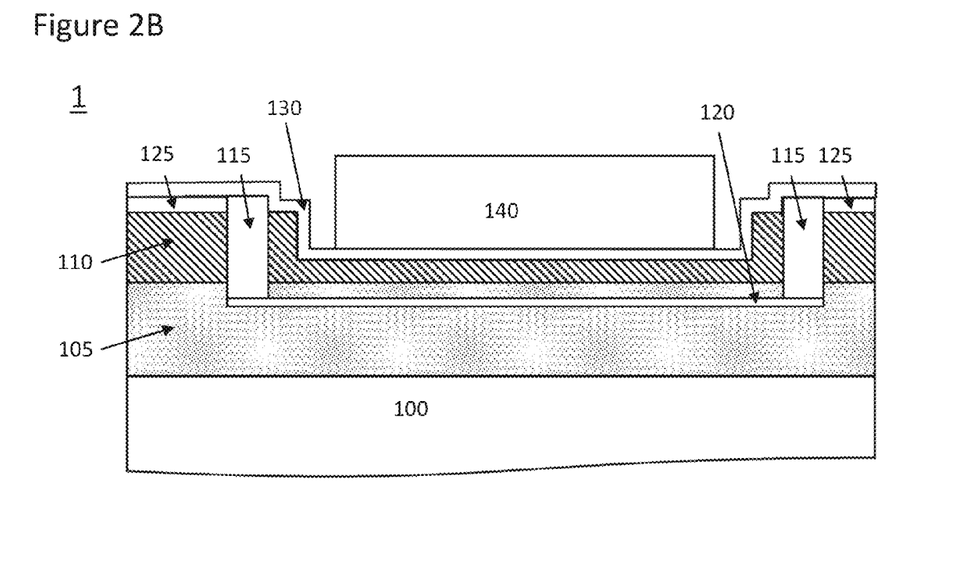

FIG. 2B shows another AlGaN/GaN 2DEG-based sensor 1 according to some other embodiments, comprising a substrate layer 100, a GaN layer 105, a AlGaN layer 110, Ohmic contacts 115, a 2DEG channel 120, electrical metallizations 125, a dielectric layer 130 and an extended gate material 140.

The sensor 1 of FIG. 2B is similar to the sensor 1 described above with respect to FIG. 2A, except that the sensor 1 of FIG. 2B further comprises a dielectric layer 130 between the AlGaN layer 110 and the extended gate material 140. The dielectric layer 130 advantageously configured to prevent leakage currents to flow between the skin—extended gate material 140 and the 2DEG channel 120. According to an exemplary embodiment, the dielectric layer 130 may have a thickness selected to be between about 3 nm and about 10 nm, and may comprise a suitable dielectric material including, for example, of an aluminium oxide ($AlO_x$). Furthermore, the dielectric layer 130 advantageously allows the usage of gate pre-biasing mode. According to an exemplary embodiment, in order to improve the electric-field sensitivity of the transistor (2DEG conductivity change in dependence on the gate material voltage) the extended gate material 140 may be biased under some electric potential.

In some embodiments, the presence of an additional or natural conductive liquid (e.g., sweat) provided on top of the AlGaN-layer 110 may create an electrochemical double layer formation at the AlGaN/Liquid-interface. This double layer comprises negative and positive ionic layers directly interacting with AlGaN surface donor states creating a charge neutrality with AlGaN-surface potential. Hence, ions and double layer formation are very sensitive to an external charge and the liquid is strongly enhances the charge response.

Figure 2C:
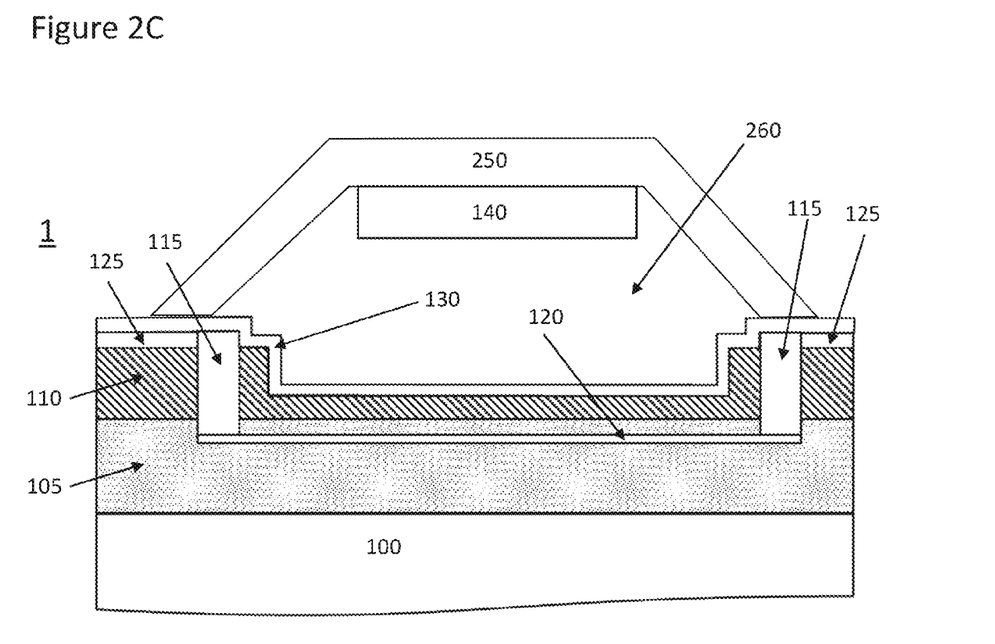

FIG. 2C shows an AlGaN/GaN 2DEG-based sensor 1 similar to the sensor 1 described above with respect to FIG. 2B, except that the sensor 1 of FIG. 2C further comprises a medium-filled cavity 260, which can be filled with a suitable medium, e.g., air, inert gas or a liquid, and a cavity closure element 250. According to an exemplary embodiment, the medium-filled cavity 260 is filled with nitrogen or an electrolyte. According to an exemplary embodiment, the cavity closure element 250 can comprise the same material as the extended gate material 140, or can comprise a conductive polymer, such as for example, rubber. The sensor 1 can additionally comprise an extended gate material 140 formed on an inner surface of the closure element 250. According to the illustrated embodiment, the sensor 1 comprises a dielectric layer 130 similar to the sensor 1 of FIG. 2B. According to some other embodiments, however, the dielectric layer 130 can be omitted. Advantageously, the cavity closure element 250 removes parasitic charges that may trap at the AlGaN/electrolyte interface during charge detection.

Figure 3:
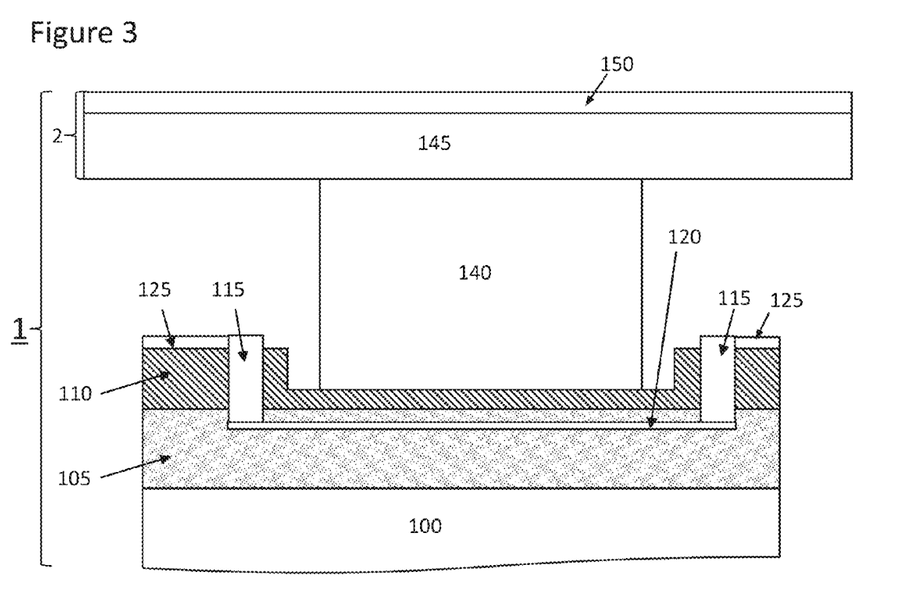
FIG. 3 illustrates an AlGaN/GaN 2DEG-based sensor according to yet some other embodiments.

FIG. 3 shows an AlGaN/GaN 2DEG-based sensor 1 according yet some other embodiments, comprising a substrate layer 100, a GaN layer 105, a AlGaN layer 110, Ohmic contacts 115, a 2DEG channel 120, electrical metallizations 125, an extended gate material 140 and an electrode stack 2.

The sensor 1 of FIG. 3 is similar to the sensor 1 described above with respect to FIG. 2A, except that the sensor 1 of FIG. 3 further comprises, an electrode stack 2 formed over the extended gate material 140, e.g., on a top surface of the extended gate material 140. The electrode stack 2 is configured to be coupled to a body skin point within a sufficiently close proximity such that, during an electrophysiological heart function polarization cycle, the electrical body charge interacts with the 2DEG channel and causes a conductivity of the 2DEG 120 channel to change. According to an exemplary embodiment, the electrode stack 2 may comprise a first layer of 145 comprising a suitable electrode material, e.g., Ag, and a second layer of 150 comprising another suitable electrode4 material, e.g., Ag/AgCl. The electrode stack 2 advantageously increases the charge transfer from the skin to the AlGaN surface. According to an exemplary embodiment, the extended gate material 140 may have a thickness selected to be between about 1 nm and about 1000 nm. According to another exemplary embodiment, the sensor 1 of FIG. 3 may comprise a dielectric layer 130 (not shown) between the AlGaN layer 110 and the extended gate material 140, similar to the sensor described above with respect to FIG. 2C.

Figure 4:
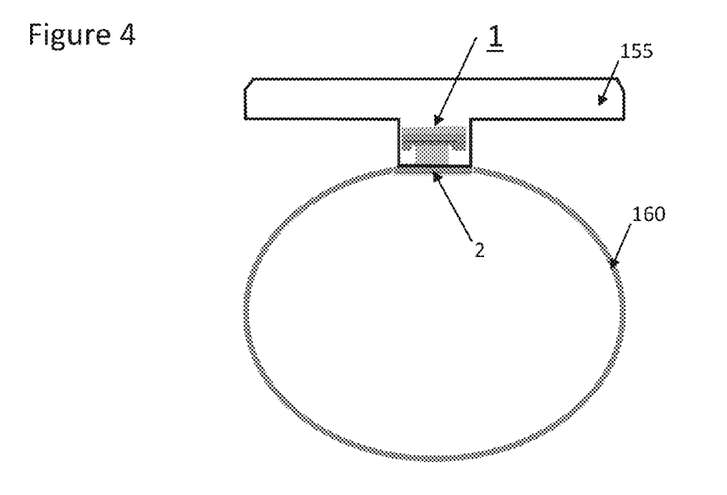
FIG. 4 illustrates a device for ECG sensing according to some embodiments.

FIG. 4 shows a schematic view of an exemplary device for ECG sensing comprising a sensor 1 according to some embodiments. The illustrated embodiment depicts schematically an exemplary wrist worn watch-like device for ECG sensing, comprising a watch-like chassis 155 and a bracelet 160. According to an exemplary embodiment, the watch-like chassis 155 provides mechanical protection and comprises control and readout circuitry for the sensor 1 similar to the sensor 1 described above with respect to FIG. 3. According to an exemplary embodiment, the electrode stack 2 is integrated in the bracelet 160 and configured to be placed sufficiently close, e.g., in direct contact with, the body skin such that an ECG-pulse can be detected.

Figure 5:
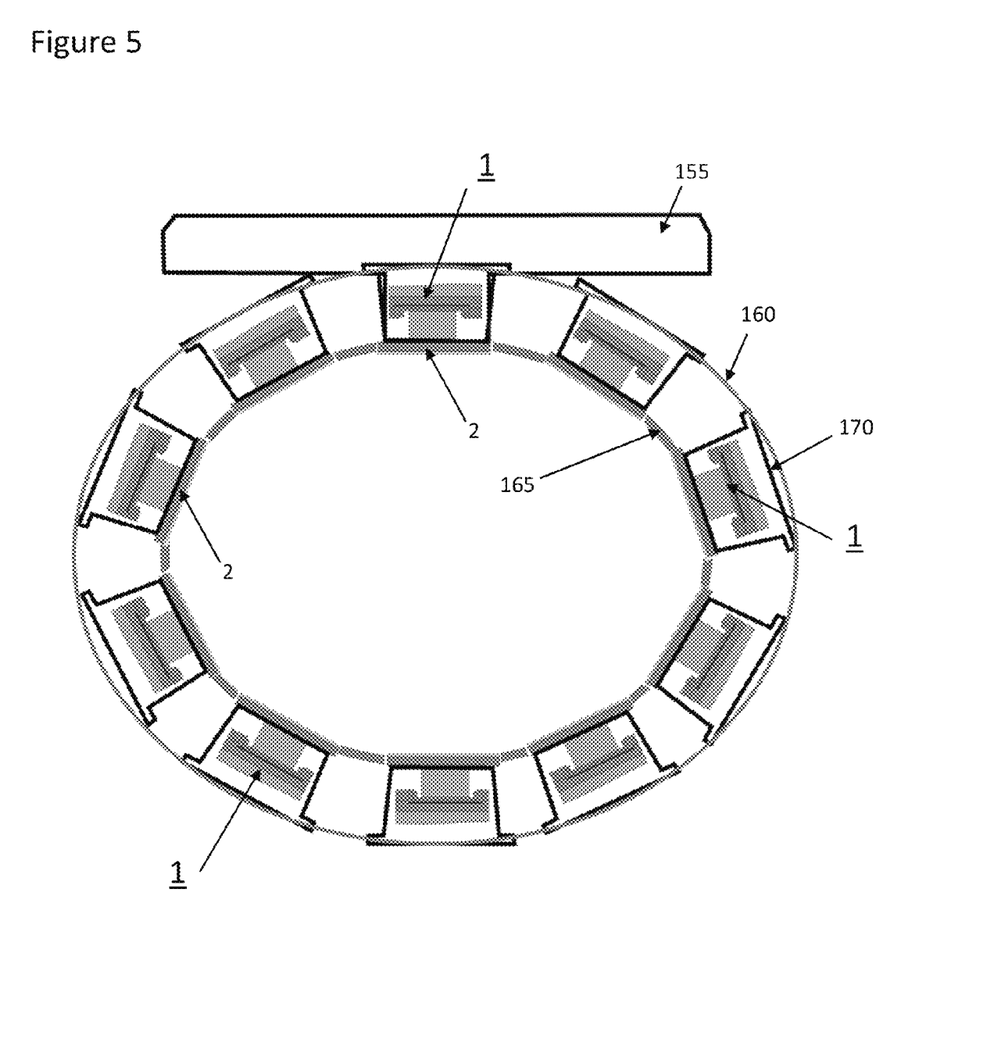
FIG. 5 illustrates a device for ECG sensing according to some other embodiments.

FIG. 5 shows a schematic view of another exemplary device for ECG sensing comprising a sensor 1 according to some embodiments. The illustrated embodiment depicts schematically an exemplary wrist worn watch-like device for ECG sensing, comprising a watch-like chassis 155 and a bracelet 160. According to an exemplary embodiment, the bracelet 160 comprises at least one container 170 configured for providing mechanical protection and a control and readout circuitry for the sensor 1 similar to the sensor 1 described above with respect to FIG. 3. According to an exemplary embodiment, the bracelet 160 comprises circuitry configured for connecting a plurality of sensors 1 in series. According to an exemplary embodiment, the electrode stack 2 of each sensor 1 is integrated in the inner side 165 of the bracelet 160 and configured to be placed sufficiently close or in direct contact with the body skin such that an ECG-pulse can be detected.

Figure 6:
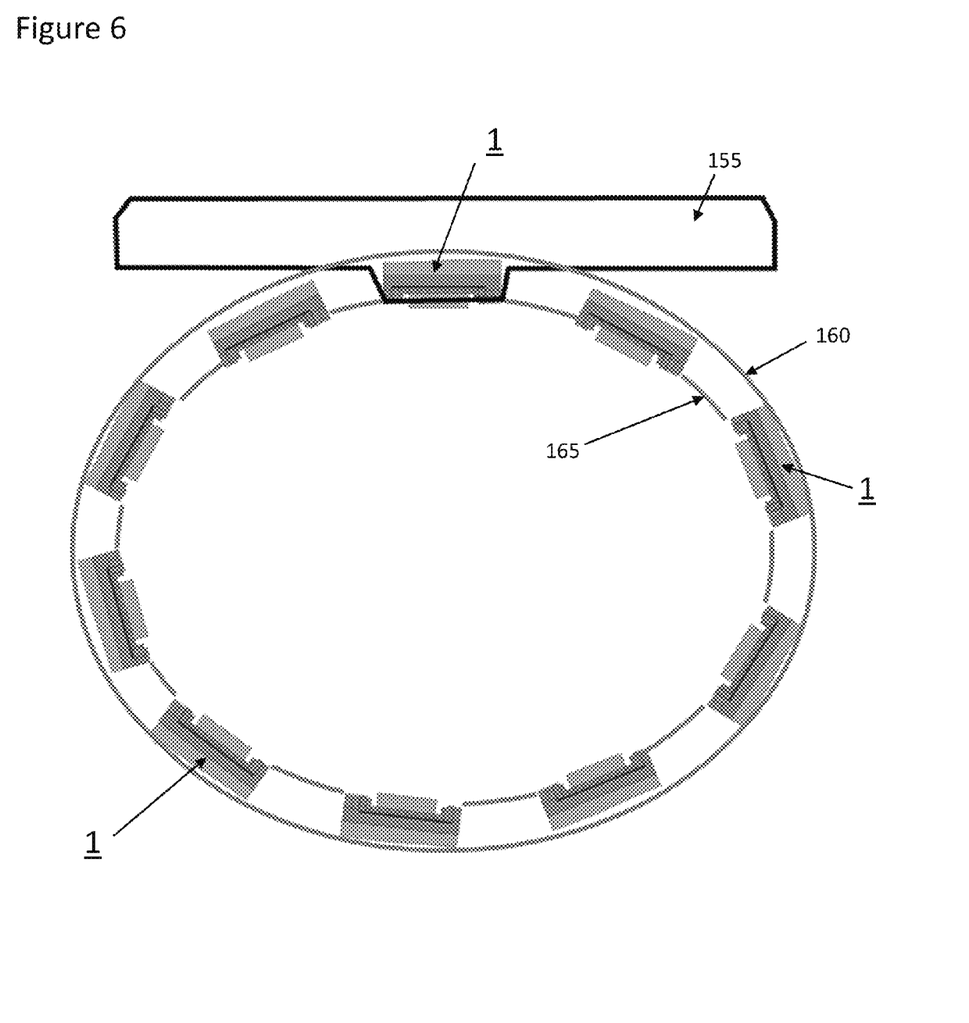
FIG. 6 illustrates a device for ECG sensing according to some other embodiments.

FIG. 6 shows a schematic view of a further exemplary device for ECG sensing comprising a sensor 1 according to some embodiments. The illustrated embodiment depicts schematically an exemplary wrist worn watch-like device for ECG sensing, comprising a watch-like chassis 155 and a bracelet 160 and plurality of sensors 1 similar to the sensor 1 described above with respect to FIG. 2A or 2B with the extended gate material 140 facing to the inner side 165 of the bracelet 160 and configured to be placed sufficiently close or in direct contact with the body skin such that ECG-pulse detection is achieved.

Figure 7:
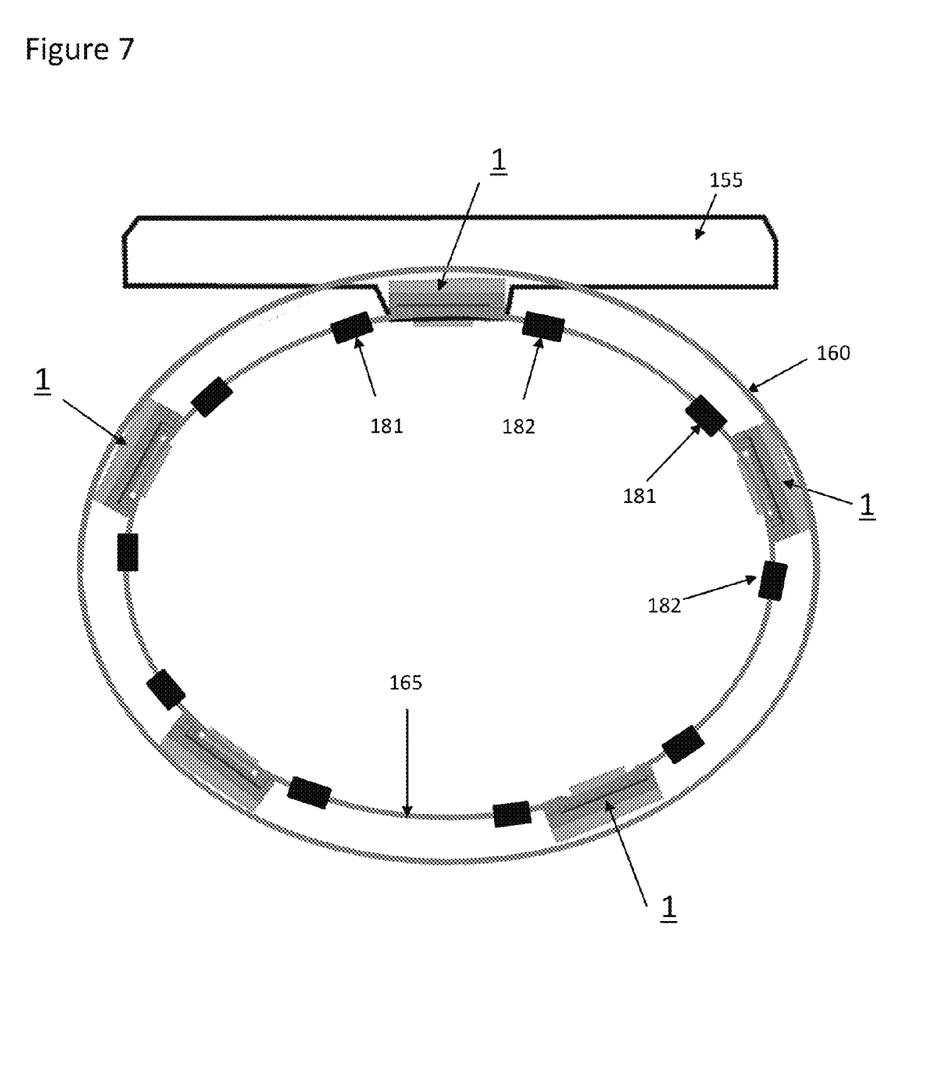
FIG. 7 illustrates a device for ECG sensing according to some other embodiments.
Figure 8:
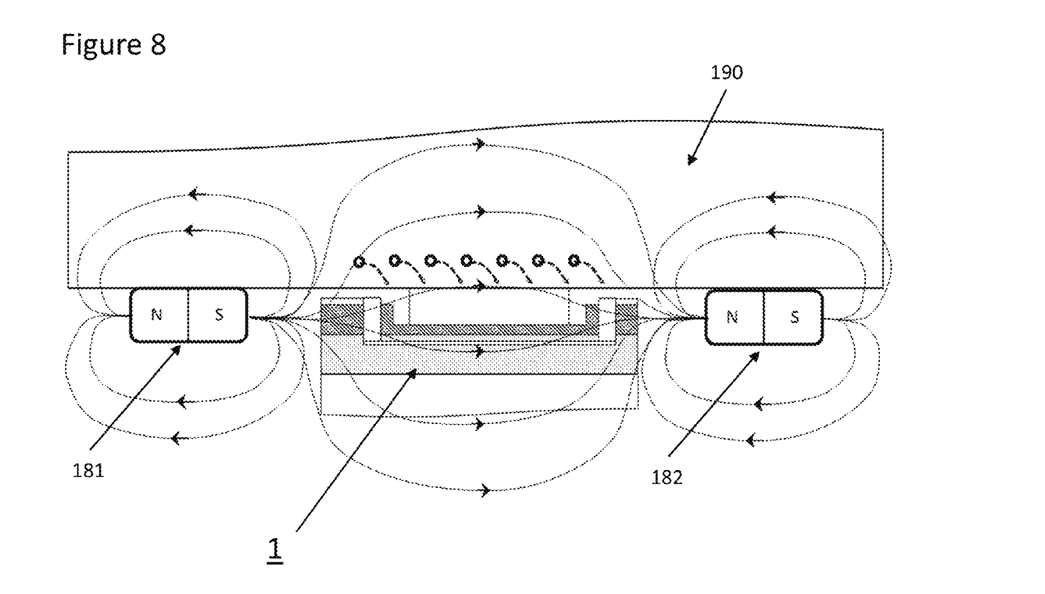
FIG. 8 illustrates the device of FIG. 7 in greater detail according to some embodiments.

FIG. 7 shows a schematic view of a further exemplary device for ECG sensing comprising a sensor 1 according to some embodiments. The illustrated embodiment depicts schematically an exemplary wrist worn watch-like device for ECG sensing, comprising a watch-like chassis 155 and a bracelet 160 and plurality of sensors 1 similar to the sensor 1 described above with respect to FIG. 2A or 2B with the extended gate material 140 facing to the inner side 165 of the bracelet 160 and configured to be placed sufficiently close or in direct contact with the body skin such that ECG-pulse detection is achieved. Additionally, one or more of the sensors 1 may be under the influence a magnetic field. According to an exemplary embodiment, the magnetic field also interacts with the intra/extra cellular ionic currents during the ECG-peak. According to an exemplary embodiment, as shown in FIG. 8, the magnetic field is placed such that, due to Lorentz force, the trajectories of the ions close to the skin surface 190 are deflected towards the skin/sensor interface, thus advantageously intensifying the interaction and increasing the sensitivity to body potential detection. According to an exemplary embodiment, such magnetic field is created by first and second magnetic elements, 181 and 182 respectively, located in the vicinity of the sensor 1. According to an exemplary embodiment, the first and second magnetic elements, 181 and 182 respectively, may be permanent or electromagnetic magnets located on each side of the sensor 1.

It shall be understood that in FIGS. 5 to 7, for clarity reasons, not all reference signs to the same represented elements have been specifically shown, but is clear that the same represented elements shall be considered as having the same reference sign, when not specifically shown. It shall also be understood that although the exemplary embodiments of FIGS. 4 to 7 refer to an exemplary device for ECG sensing with wrist-worn form, the sensor 1 according to any of the embodiments of the invention may be integrated in a device for ECG sensing with a patch-worn form. As shown in FIGS. 5 to 7, a plurality of sensor elements 1 may be connected in series (or in parallel) in such patch-worn device for ECG sensing.

Figure 9A:
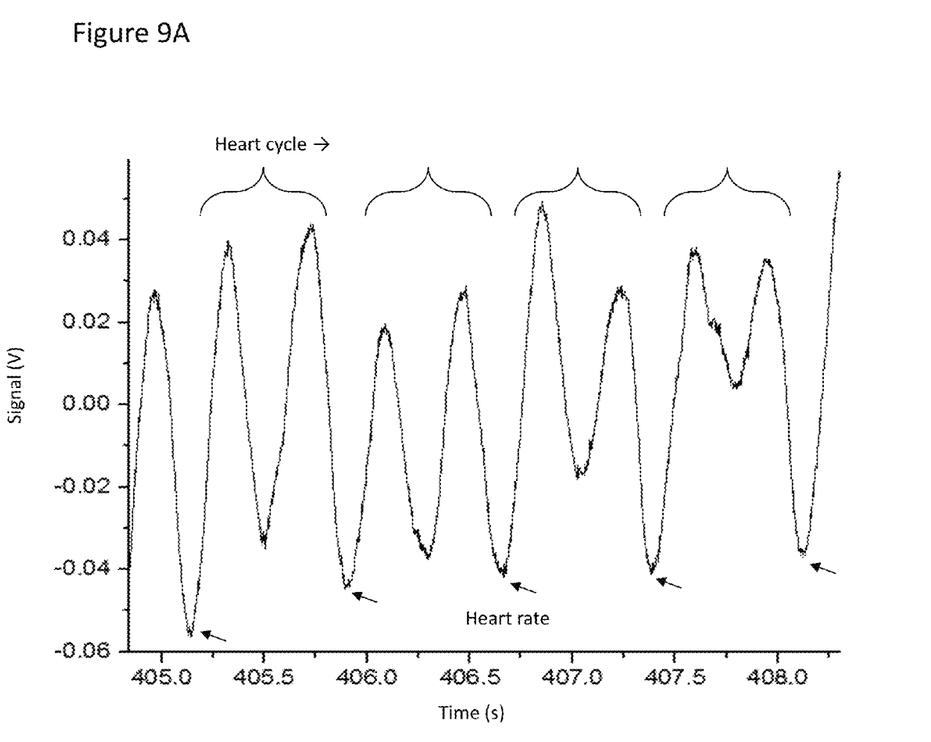
FIGS. 9A to 9C illustrate a heart charge-based ECG-time equivalent signal measurement using an AlGaN/GaN 2DEG-based sensor according to some embodiments.
Figure 9B:
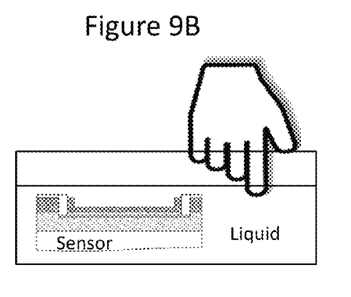
Figure 9C:
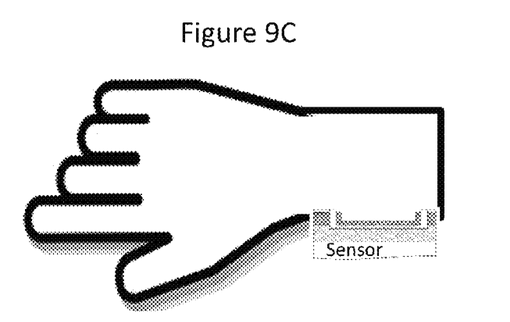

FIG. 9A shows a heart charge-based ECG-time equivalent signal measured at a single body point using an AlGaN/GaN 2DEG-based sensor, according to some embodiments. The illustrated heart charge-based ECG-time equivalent signal of FIG. 9A corresponds to a measurement made on a wrist using an exemplary sensor configuration as shown in FIG. 9C. A heart charge-based ECG-time equivalent signal similar to FIG. 9A can also be obtained using a configuration shown in FIG. 9B, where the sensor is placed in a conductive liquid solution.

Figure 10A:
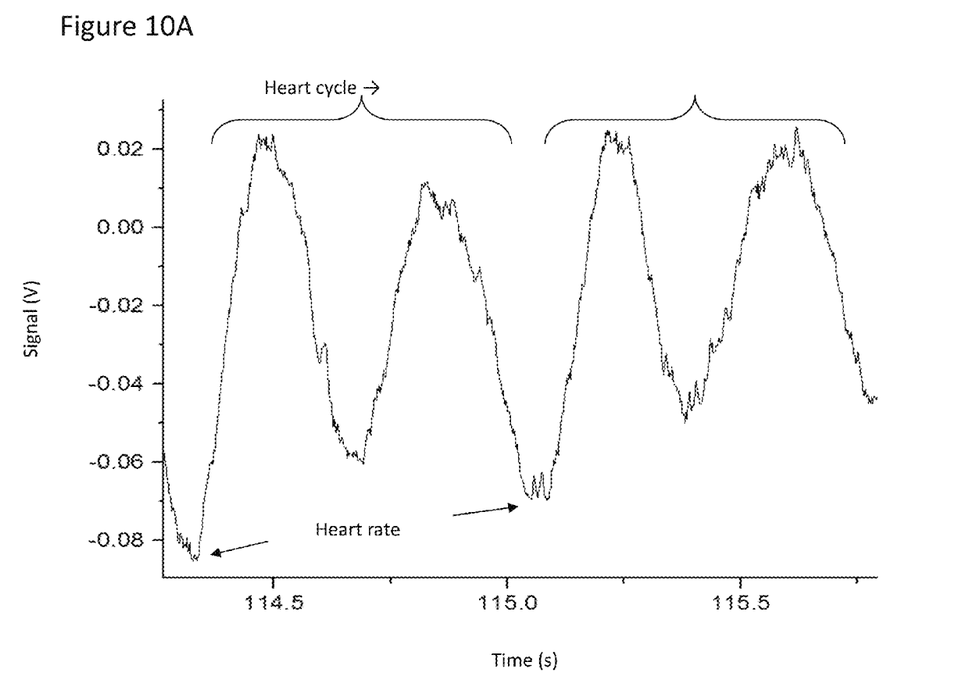
FIGS. 10A and 10B illustrate a heart charge-based ECG-time equivalent signal measurement using an AlGaN/GaN 2DEG-based sensor according to some other embodiments.
Figure 10B:
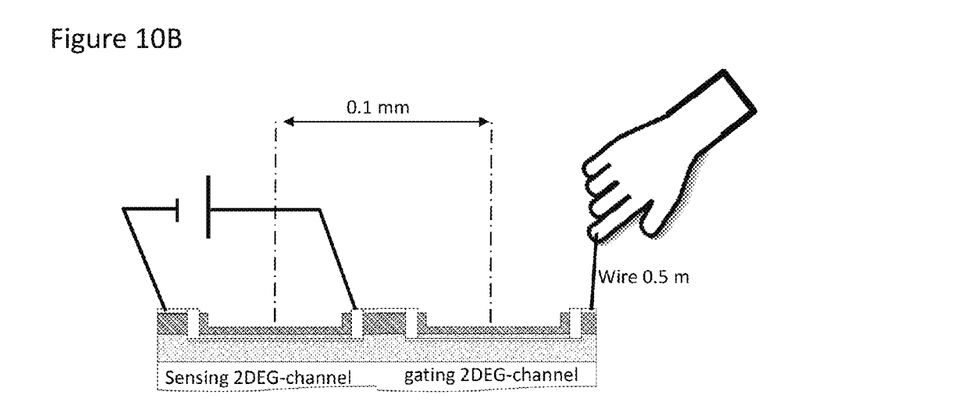

FIG. 10A shows a heart charge-based ECG-time equivalent signal measured at single body point using an AlGaN/GaN 2DEG-based sensor, according to some other embodiments. The illustrated heart charge-based ECG-time equivalent signal of FIG. 10A corresponds a measurement made using an exemplary sensor configuration as shown in FIG. 10B, comprising an additional 2DEG-channel acting as an external charge gating electrode providing electrical connection to the body. According to an exemplary embodiment, the second gating-2DEG-channel is patterned within the same GaN/AlGaN-substrate.

Figure 11A:
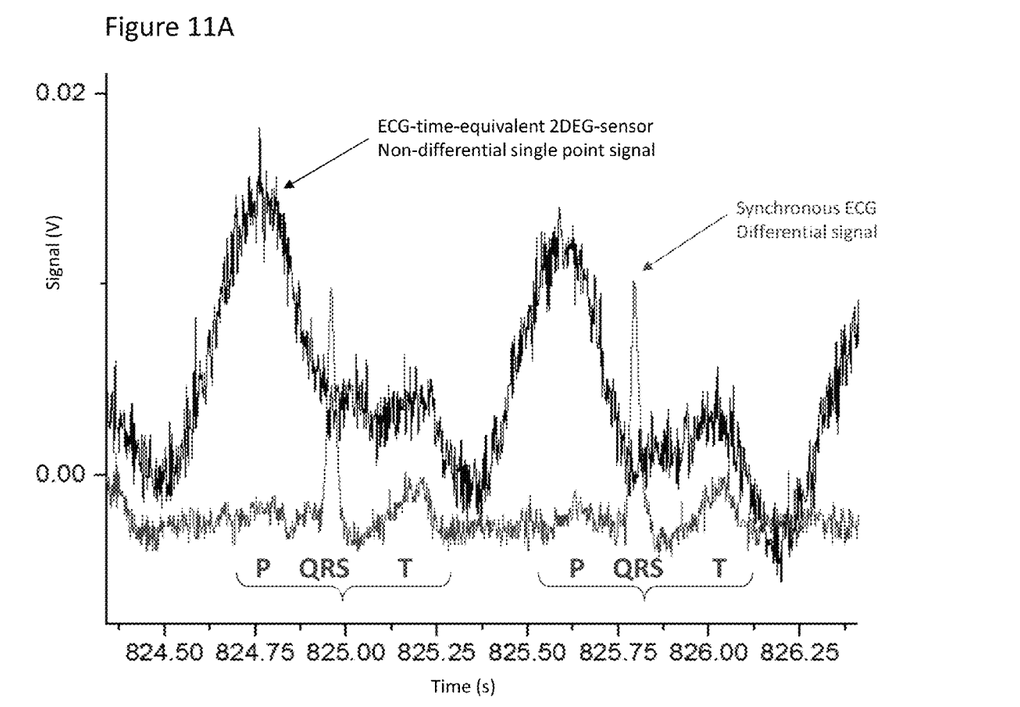
FIGS. 11A and 11B illustrate a heart charge-based ECG-time equivalent signal measurement using an AlGaN/GaN 2DEG-based sensor according to yet some other embodiments.
Figure 11B:
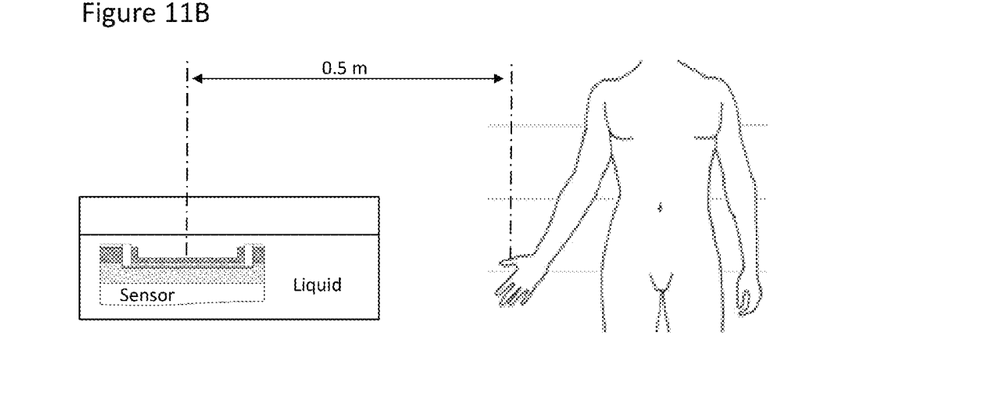

FIG. 11A shows a heart charge-based ECG-time equivalent signal measured at single body point using an AlGaN/GaN 2DEG-based sensor, according to some other embodiments. The illustrated heart charge-based ECG-time equivalent signal of FIG. 11A is synchronized with a standard differential ECG-signal measured at a 0.5 meter distance from the body skin using an exemplary sensor configuration shown in FIG. 11B, where the sensor is placed into a conductive liquid solution.

Advantageously, according to some embodiments, the sensor includes a charge high sensitivity open gate, passivation-free recessed (or ultrathin grown) 2DEG-based HEMT. The sensors have a charge sensitivity that is sufficiently high such that it is able to detect smallest electrical charges (in the pC range) at distances of dozens of centimeters. According to an exemplary embodiment, if the sensor is immersed into an ion conductive liquid, then the liquid ions will electro-dynamically react to any external charge by their movement and being in direct contact to the AlGaN-surface the charge sensitivity is very much enhanced. The liquid functions in this situation as an additional sensor functionalization-antenna perfectly matched to a 2DEG-transducer. The heart generates electric charges (of few pC) and a superposition dipole of them is projected to a liquid antenna in which the sensor is immersed in. If the body surface point is in physical contact with liquid the sensed signal is the biggest, because the electric field within body is transferred to the liquid with minimal loses. If the body surface point is outside of the liquid then the inner-body electric field created by the heart is much weaker transmitted to the liquid but its detection until a critical distance (around 50 cm in a Faraday room) remains possible.

Further advantageous embodiments are possible. For example, according to an exemplary embodiment, the device for ECG sensing may also use the detected heart charges dynamics, which is fully time equivalent with P-QRS-T-wave to calculate a blood pressure (BP) value. According to an exemplary embodiment, the calculated BP value comprises a real-time value. According to an exemplary embodiment, the device for ECG sensing comprises further comprises HW and/or SW computing means for determining the blood pressure based on a time difference between the heart charge-pulse and a measured palpatoric (mechanic) conventional heart rate. The length of this time (Palpatoric delay) can define the systolic and diastolic blood pressure values by means of known Pulse-Transit-Time (PTT) techniques. According to an exemplary embodiment, the palpatoric (blood motion based) heart rate may be also measure by means of Photo-plethysmographic (Pulse-Oxymetric) heart rate measurements.

The foregoing description details certain embodiments of the disclosure. It will be appreciated, however, that no matter how detailed the foregoing appears in text, the disclosure may be practiced in many ways. It should be noted that the use of particular terminology when describing certain features or aspects of the disclosure should not be taken to imply that the terminology is being re-defined herein to be restricted to including any specific characteristics of the features or aspects of the disclosure with which that terminology is associated.

What is claimed is:

1. A sensor comprising:
   a substrate;
   a GaN/AlGaN hetero junction structure formed on the substrate and configured to form a two-dimensional electron gas (2DEG) channel within the GaN/AlGaN hetero-junction structure;
   Ohmic contacts connected to electrical metallizations and partly extending through the GaN/AlGaN hetero junction structure to directly contact the 2DEG channel, wherein a recess is formed in the GaN/AlGaN hetero junction structure between the Ohmic contacts; and
   a dielectric layer formed on a top surface of the sensor and over the recess, the dielectric layer extending to cover the Ohmic contacts and the electrical metallizations.

2. The sensor according to claim 1, further comprising an extended gate material formed on a top surface of the dielectric layer and in the recess of the GaN/AlGaN hetero junction structure.

3. The sensor according to claim 1, further comprising a cavity closure element configured to enclose a cavity formed between the cavity closure element and a top surface of the of the dielectric layer, wherein the cavity is configured to be filled with a liquid.

4. A method of using the sensor according to claim 1 for ECG detection, comprising applying the sensor in sufficiently close proximity to a single body skin point such that, during an electrophysiological heart function polarization cycle, the electrical body charge interacts with the 2DEG channel and causes a conductivity of the 2DEG channel to change.

5. The sensor according to claim 2, further comprising an electrode stack formed on a top surface of the extended gate material.

6. The sensor according to claim 3, wherein the cavity closure element is formed of a conductive polymer.

7. The sensor according to claim 3, wherein the cavity is filed with one of nitrogen gas or an electrolyte.

8. The device according to claim 4, wherein applying the sensor in sufficiently close proximity to the single body skin point comprises applying the sensor in direct contact with the single body skin point.

9. A device for ECG sensing comprising:
   at least one sensor each according to the sensor of claim 5, wherein the at least one sensor is arranged so that one of the recess of the GaN/AlGaN hetero junction structure, the extended gate material or the electrode stack is configured to be coupled to a body skin point within a sufficiently close proximity such that, during an electrophysiological heart function polarization cycle, the electrical body charge interacts with the 2DEG channel and causes a conductivity of the 2DEG channel to change.

10. A method for detecting a signal associated with an electrocardiogram (ECG), comprising:
    applying the sensor according to claim 5 such that one of the recess of the GaN/AlGaN hetero junction structure, the extended gate material or the electrode stack is in direct contact or sufficiently close to a certain living being's body skin point, such that the body charge interacts with the sensor's 2DEG channel; and
    detecting a conductivity change within the 2DEG channel during an electrophysiological heart polarization cycle of a living being.

11. The sensor according to claim 6, wherein the cavity further comprises an extended gate material formed on an inner surface of the cavity closure element.

12. The device according to claim 9, wherein the at least one sensor is configured such that one of the GaN/AlGaN hetero junction recessed area, the extended gate material or the electrode stack is configured to be in direct contact with the body skin point.

13. The device according to claim 9, wherein the body skin point comprises a single body skin point.

14. The device according to claim 9, wherein the ECG sensing comprises a charge-based non-differential ECG sensing.

15. The device according to claim 9, comprising a plurality of sensors according to claim 1 connected in series or in parallel and configured for combined ECG detection.

16. The device according to claim 9, wherein the at least one sensor is configured to be under the influence of a magnetic field.

17. The device according to claim 9 further configured for calculating a blood pressure value based on ECG detection.

18. A patch-worn or a wrist-worn apparatus comprising the device according to claim 9.

19. The method according to claim 10, wherein detecting the signal associated with the ECG comprises detecting a signal associated with a charge-based non-differential ECG.

20. The device according to claim 15, further configured for noise cancellation.

* * * * *

UNITED STATES PATENT AND TRADEMARK OFFICE
CERTIFICATE OF CORRECTION

PATENT NO. : 9,675,262 B2
APPLICATION NO. : 14/265088
DATED : June 13, 2017
INVENTOR(S) : Roman Vitushinsky et al.

It is certified that error appears in the above-identified patent and that said Letters Patent is hereby corrected as shown below:

In Column 2 at Line 43, Change "that that" to --that--.

In Column 9 at Lines 64-65, In Claim 1, change "hetero junction" to --hetero-junction--.

In Column 9 at Lines 66-67, In Claim 1, change "hetero junction" to --hetero-junction--.

In Column 10 at Lines 6-7 (approx.), In Claim 2, change "hetero junction" to --hetero-junction--.

In Column 10 at Line 10 (approx.), In Claim 3, after "surface" delete "of the".

In Column 10 at Line 35 (approx.), In Claim 9, change "hetero junction" to --hetero-junction--.

In Column 10 at Line 47, In Claim 10, change "hetero junction" to --hetero-junction--.

In Column 10 at Line 60, In Claim 12, change "hetero junction" to --hetero-junction--.

Signed and Sealed this
Twenty-fourth Day of October, 2017

Joseph Matal
*Performing the Functions and Duties of the
Under Secretary of Commerce for Intellectual Property and
Director of the United States Patent and Trademark Office*